(12) United States Patent
Liu (10) Patent No.: US 10,470,858 B2
(45) Date of Patent: Nov. 12, 2019

(54) REMOVABLE BRUSH HEAD FOR AN ELECTRIC TOOTHBRUSH

(71) Applicant: JS Holding Inc., Dover, DE (US)

(72) Inventor: Xinlan Liu, Chongqing (CN)

(73) Assignee: JS Holding Inc., Dover, DE (US)

( * ) Notice: Subject to any disclaimer, the term of this patent is extended or adjusted under 35 U.S.C. 154(b) by 73 days.

(21) Appl. No.: 15/701,797

(22) Filed: Sep. 12, 2017

(65) Prior Publication Data
US 2019/0015183 A1 Jan. 17, 2019

(30) Foreign Application Priority Data
Jul. 11, 2017 (CN) .......................... 2017 1 0559758

(51) Int. Cl.
| | |
|---|---|
| A61C 17/34 | (2006.01) |
| A61C 17/22 | (2006.01) |
| A46B 5/00 | (2006.01) |
| A46B 15/00 | (2006.01) |
| A46B 9/04 | (2006.01) |
| A61C 15/04 | (2006.01) |

(52) U.S. Cl.
CPC .......... *A61C 17/222* (2013.01); *A46B 5/0095* (2013.01); *A46B 9/04* (2013.01); *A46B 15/0071* (2013.01); *A61C 17/22* (2013.01); *A61C 17/34* (2013.01); *A61C 17/3427* (2013.01); *A61C 17/3436* (2013.01); *A61C 15/046* (2013.01)

(58) Field of Classification Search
CPC ... A61C 17/22; A61C 17/221; A61C 17/3481; A61C 17/3427; A61C 17/34
See application file for complete search history.

(56) References Cited

U.S. PATENT DOCUMENTS

| | | |
|---|---|---|
| D297,784 S | 9/1988 | Moret |
| D361,433 S | 8/1995 | Yang |
| 5,577,285 A * | 11/1996 | Drossler ............ A61C 17/3436 15/22.1 |
| D385,702 S | 11/1997 | Okada |
| 5,974,615 A * | 11/1999 | Schwarz-Hartmann ..................... A61C 17/3472 15/22.1 |

(Continued)

FOREIGN PATENT DOCUMENTS

| | | |
|---|---|---|
| EP | 2550938 A1 | 1/2013 |
| JP | 2016152936 A | 8/2016 |

(Continued)

*Primary Examiner* — Michael D Jennings
(74) *Attorney, Agent, or Firm* — Fox Rothschild LLP (57) ABSTRACT

A removable toothbrush head for an electric toothbrush includes a bristle carrier and an elongated neck. One end portion of the elongated neck includes an opening for connection to an electric toothbrush handle, and another end portion comprises a neck hub configured to rotatably support the bristle carrier. Also included is a driven brush shaft disposed longitudinally within the elongated neck. The brush shaft is configured to interact with the bristle carrier at a distal end portion of the brush shaft, which includes a pivot extension extending therefrom and spaced apart from the longitudinal axis of the brush shaft, as well as a bristle carrier interface positioned at least partially along the longitudinal axis of the brush shaft and configured to cause partial rotational motion of the bristle carrier when the brush shaft is driven by an electric toothbrush handle.

14 Claims, 9 Drawing Sheets

(56) References Cited

U.S. PATENT DOCUMENTS

| | | | |
|---|---|---|---|
| 6,018,840 A | 2/2000 | Guay et al. | |
| 6,021,538 A | 2/2000 | Kressner et al. | |
| 6,058,541 A | 5/2000 | Masterman et al. | |
| 6,094,769 A | 8/2000 | Driesen et al. | |
| 6,141,819 A | 11/2000 | Driesen et al. | |
| 6,195,828 B1* | 3/2001 | Fritsch | A61C 17/222 15/22.1 |
| 6,308,359 B2 | 10/2001 | Fritsch et al. | |
| D452,775 S | 1/2002 | Wright | |
| 6,349,442 B1 | 2/2002 | Cohen et al. | |
| D455,556 S | 4/2002 | Kling | |
| 6,367,108 B1 | 4/2002 | Fritsch et al. | |
| D459,892 S | 7/2002 | Eliav et al. | |
| 6,475,553 B2 | 11/2002 | Guay et al. | |
| D474,894 S | 5/2003 | Ferber et al. | |
| D475,529 S | 6/2003 | Wright et al. | |
| 6,588,042 B2 | 7/2003 | Fritsch et al. | |
| 6,665,901 B2 | 12/2003 | Driesen et al. | |
| D487,636 S | 3/2004 | De Salvo | |
| D489,534 S | 5/2004 | Hensel | |
| 6,785,929 B2 | 9/2004 | Fritsch et al. | |
| 6,871,373 B2 | 3/2005 | Driesen et al. | |
| D526,487 S | 8/2006 | Chenvainu et al. | |
| D527,185 S | 8/2006 | Vu | |
| D527,905 S | 9/2006 | Winkler | |
| D579,664 S | 11/2008 | Fisher et al. | |
| D599,555 S | 9/2009 | Oliphant | |
| D600,920 S | 9/2009 | Yeh | |
| D607,646 S | 1/2010 | Ino | |
| D611,712 S | 3/2010 | Stoerkel et al. | |
| D612,611 S | 3/2010 | Brown, Jr. et al. | |
| 7,690,067 B2 | 4/2010 | Schaefer et al. | |
| 7,941,886 B2 | 5/2011 | Chenvainu et al. | |
| D643,218 S | 8/2011 | Wagner | |
| D648,539 S | 11/2011 | Wai | |
| D648,941 S | 11/2011 | Leung | |
| 8,209,808 B2 | 7/2012 | Kressner | |
| 8,220,097 B2 | 7/2012 | DePuydt et al. | |
| 8,336,155 B2* | 12/2012 | Crossman | A61C 17/3463 15/167.1 |
| D676,660 S | 2/2013 | Crossman | |
| 8,453,288 B2 | 6/2013 | Driesen et al. | |
| D688,045 S | 8/2013 | Key et al. | |
| D688,464 S | 8/2013 | Hara | |
| D689,698 S | 9/2013 | Dickie et al. | |
| D696,023 S | 12/2013 | Gebski | |
| 8,621,698 B2 | 1/2014 | Chenvainu et al. | |
| 8,631,532 B2* | 1/2014 | Utsch | A61C 17/3436 15/22.1 |
| 8,661,597 B2* | 3/2014 | Kressner | A61C 17/3472 15/22.1 |
| 8,782,841 B2* | 7/2014 | Sale | A61C 17/222 15/22.1 |
| 8,813,292 B2 | 8/2014 | Driesen et al. | |
| D719,737 S | 12/2014 | Adriaenssen et al. | |
| D743,173 S | 11/2015 | Sohn | |
| 9,204,948 B2* | 12/2015 | Kloster | A61C 17/222 |
| D747,609 S | 1/2016 | Watkins | |
| 9,226,808 B2* | 1/2016 | Utsch | A61C 17/222 |
| D751,821 S | 3/2016 | Since | |
| D759,380 S | 6/2016 | Watkins | |
| D759,381 S | 6/2016 | Watkins | |
| D759,383 S | 6/2016 | Watkins | |
| 9,392,867 B2 | 7/2016 | Bresselschmidt | |
| 9,420,877 B2 | 8/2016 | Wen et al. | |
| D766,580 S | 9/2016 | Kollar et al. | |
| 9,439,741 B2* | 9/2016 | Dishon | A61C 17/222 |
| D767,895 S | 10/2016 | Stebila et al. | |
| D769,626 S | 10/2016 | Bloch et al. | |
| 9,468,511 B2* | 10/2016 | Garrigues | A61C 17/3481 |
| D771,952 S | 11/2016 | Sedic | |
| D773,192 S | 12/2016 | Nabavi | |
| D773,822 S | 12/2016 | Sikora et al. | |
| D774,772 S | 12/2016 | Sedic | |
| D774,773 S | 12/2016 | Sedic | |
| D775,469 S | 1/2017 | Sikora et al. | |
| D775,836 S | 1/2017 | Sedic | |
| D776,438 S | 1/2017 | Sedic | |
| D778,057 S | 2/2017 | Sohn | |
| D780,455 S | 3/2017 | Kandemir | |
| D787,189 S | 5/2017 | Fretwell et al. | |
| D794,336 S | 8/2017 | Zavalloni | |
| D795,590 S | 8/2017 | Sedic | |
| 9,724,180 B1* | 8/2017 | Liu | A61C 17/222 |
| D799,217 S | 10/2017 | Massee | |
| D799,218 S | 10/2017 | Okai | |
| D799,835 S | 10/2017 | Okai | |
| D801,696 S | 11/2017 | McGarry et al. | |
| 9,827,079 B1 | 11/2017 | Liu | |
| D805,306 S | 12/2017 | Massee | |
| 9,987,109 B2* | 6/2018 | Sokol | A61C 17/0202 |
| 2002/0100134 A1 | 8/2002 | Dunn et al. | |
| 2002/0157198 A1 | 10/2002 | Biro et al. | |
| 2003/0031979 A1 | 2/2003 | Shortt et al. | |
| 2003/0101526 A1 | 6/2003 | Hilscher et al. | |
| 2011/0010874 A1 | 1/2011 | Dickie | |
| 2013/0007969 A1 | 1/2013 | Driesen et al. | |
| 2013/0029289 A1* | 1/2013 | Utsch | A61C 17/222 433/146 |
| 2013/0133683 A1 | 5/2013 | Guthans | |
| 2013/0333126 A1 | 12/2013 | Miller | |
| 2014/0101871 A1 | 4/2014 | Chenvainu et al. | |
| 2015/0173502 A1 | 6/2015 | Sedic | |
| 2015/0245895 A1* | 9/2015 | Kressner | A61C 17/222 15/22.1 |
| 2016/0287363 A1 | 10/2016 | Miller | |
| 2016/0353869 A1 | 12/2016 | Dishon | |
| 2016/0374609 A1 | 12/2016 | Vetter et al. | |
| 2017/0042638 A1 | 2/2017 | Lee | |
| 2017/0151044 A1* | 6/2017 | Okai | A61C 17/222 |
| 2019/0069978 A1* | 3/2019 | Katano | A61C 17/225 |

FOREIGN PATENT DOCUMENTS

| | | |
|---|---|---|
| WO | 2004098444 | 11/2004 |
| WO | 2004098445 | 11/2004 |

\* cited by examiner

REMOVABLE BRUSH HEAD FOR AN ELECTRIC TOOTHBRUSH

RELATED APPLICATIONS AND CLAIM OF PRIORITY

This patent application claims priority to Chinese patent application no. 201710559758.2, filed Jul. 11, 2017.

BACKGROUND

This disclosure relates to the field of electric toothbrushes and, particularly, removable brush heads attachable to an electric toothbrush handle.

Many types of electric toothbrushes use high-speed vibrations or oscillations from a motor disposed within the toothbrush handle to drive a separately-attachable (and replaceable) brush head. In order to operate the electric toothbrush, the construction of the brush head requires that it be tightly coupled to the drive shaft of the toothbrush handle so as to withstand the high-speed vibrations during operation of the toothbrush. Many existing products, therefore, utilize metal and/or springs inside the brush head to facilitate a tight coupling to the drive shaft of the toothbrush handle and withstand the vibrational forces present during operation of the toothbrush, which limits the vibration felt by the user, as well as the noise caused by such vibration. However, use of metal, springs, gears, and/or linkages within the brush head may increase the complexity and/or cost of manufacturing the brush head. Therefore, it is desirable to make a toothbrush head with little to no use of metal, springs, gears, and/or linkages, yet still be capable of withstanding high-speed vibrations present during operation of the toothbrush.

Replacement brush heads that do not include metallic components, springs, gears, and/or complex linkages have previously been introduced in an effort to simplify and/or reduce manufacturing costs of the brush heads. For example, U.S. Pat. No. 9,439,741 discloses a replacement brush head for an electric toothbrush utilizing a drive construction having a unitary, non-metallic brush shaft configured to drive a bristle carrier into rotational and/or oscillatory motion. The brush shaft relies upon a thin eccentric extension laterally offset from the longitudinal axis of the brush shaft to interact with a V-shaped opening on the bristle carrier in order to translate the oscillatory motion imparted by the toothbrush motor into rotational and/or oscillatory movement of the bristle carrier. However, as the eccentric extension is offset from the axis of the brush shaft, the high torque experienced by the eccentric extension when interacting with the V-shaped opening of the bristle carrier may lead to excessive wear on the eccentric extension and/or bristle carrier, high vibration and noise, and, in some cases, failure of the eccentric extension portion of the brush shaft. Additionally, as the brush shaft and bristle carrier may each be unitarily formed of a non-metallic material (e.g., plastic, polyester, etc.), the wear and/or failure rates may be even more prominent.

This patent document describes an apparatus that may address at least some of the issues described above and/or other issues.

SUMMARY

In accordance with some embodiments of the disclosure, a removable toothbrush head is shown and described. The removable toothbrush head includes a bristle carrier, wherein the bristle carrier is configured to retain a plurality of brush bristles thereon, as well as an elongated neck having a proximal end portion and a distal end portion, wherein the proximal end portion of the elongated neck comprises an opening formed therein for connection of the elongated neck to an electric toothbrush handle. The distal end portion of the elongated neck comprises a neck hub positioned traverse to a longitudinal axis of the elongated neck and configured to rotatably support the bristle carrier. The removable toothbrush head also includes a brush shaft disposed longitudinally within the elongated neck. The brush shaft is configured to be removably couplable to a drive shaft of the electric toothbrush handle at an opening located within a proximal end portion of the brush shaft. The brush shaft is configured to interact with the bristle carrier at a distal end portion of the brush shaft. The distal end portion of the brush shaft comprises a pivot extension extending from the distal end portion of the brush shaft and spaced apart from the longitudinal axis of the brush shaft. The pivot extension is pivotally couplable to a pivot support within the distal end portion of the elongated neck so as to enable at least partial rotational motion of the brush shaft about the pivot extension, and a bristle carrier interface positioned at least partially along the longitudinal axis of the brush shaft. The bristle carrier interface is configured to interact with the bristle carrier to cause partial rotational motion of the bristle carrier upon the neck hub when the brush shaft is driven by the drive shaft of the electric toothbrush handle.

The removable toothbrush head may further include a sleeve inserted into the opening formed in the proximal end portion of the elongated neck. The sleeve is configured to receive and guide the drive shaft of the electric toothbrush handle into the opening formed in the proximal end of the brush shaft. The sleeve may include a cylindrical rim formed on a distal end portion thereof, wherein the cylindrical rim is configured to movably retain a proximal end portion of the brush shaft therein. Additionally and/or alternatively, the sleeve may include a deflectable retention shoulder, the deflectable retention shoulder configured to mate with a retention opening formed in the elongated neck when the sleeve is inserted into the opening formed in the proximal end portion of the elongated neck.

The bristle carrier may include a carrier extension extending from a surface opposite the plurality of brush bristles. The carrier extension may comprise a channel sized and shaped to interact with the bristle carrier interface of the brush shaft. The carrier extension may also include an inner opening and an inner surface configured to allow the carrier extension to fit over an outer surface of the neck hub. In some embodiments, the carrier extension is substantially cylindrical. Additionally, in some embodiments, the channel formed in the carrier extension may be a U-shaped channel. The U-shaped channel may be sized and contoured to receive a distal end portion of the bristle carrier interface.

The removable toothbrush head may also include a retention rod extending at least partially through the distal end portion of the elongated neck and the neck hub, wherein the carrier extension further includes a pair of elongated slots configured to receive the retention rod so as to enable restricted rotational motion of the bristle carrier about the neck hub.

In some embodiments, the brush shaft is formed as a single piece, and the brush shaft may be formed of a molded plastic material. Additionally and/or alternatively, the bristle carrier interface of the brush shaft may be one of an egg-shaped cross-sectional interface or an elliptical-shaped cross-sectional interface.

In accordance with other embodiments of the disclosure, a driving system for an electric toothbrush head is disclosed. The driving system may include a bristle carrier. The bristle carrier is configured to retain a plurality of brush bristles thereon. A brush shaft is configured to be removably couplable to a drive shaft of an electric toothbrush handle at an opening located within a proximal end portion of the brush shaft. The brush shaft is configured to interact with the bristle carrier at a distal end portion of the brush shaft. The distal end portion of the brush shaft may include a pivot extension extending from the distal end portion of the brush shaft and spaced apart from the longitudinal axis of the brush shaft. The pivot extension may be configured to enable at least partial rotational motion of the brush shaft about the pivot extension. A bristle carrier interface may be positioned at least partially along the longitudinal axis of the brush shaft. The bristle carrier interface may be configured to interact with the bristle carrier to cause partial rotational motion of the bristle carrier when the brush shaft is driven by the drive shaft of the electric toothbrush handle.

DETAILED DESCRIPTION

The following description is made for the purpose of illustrating the general principles of the present disclosure and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Figure 1:
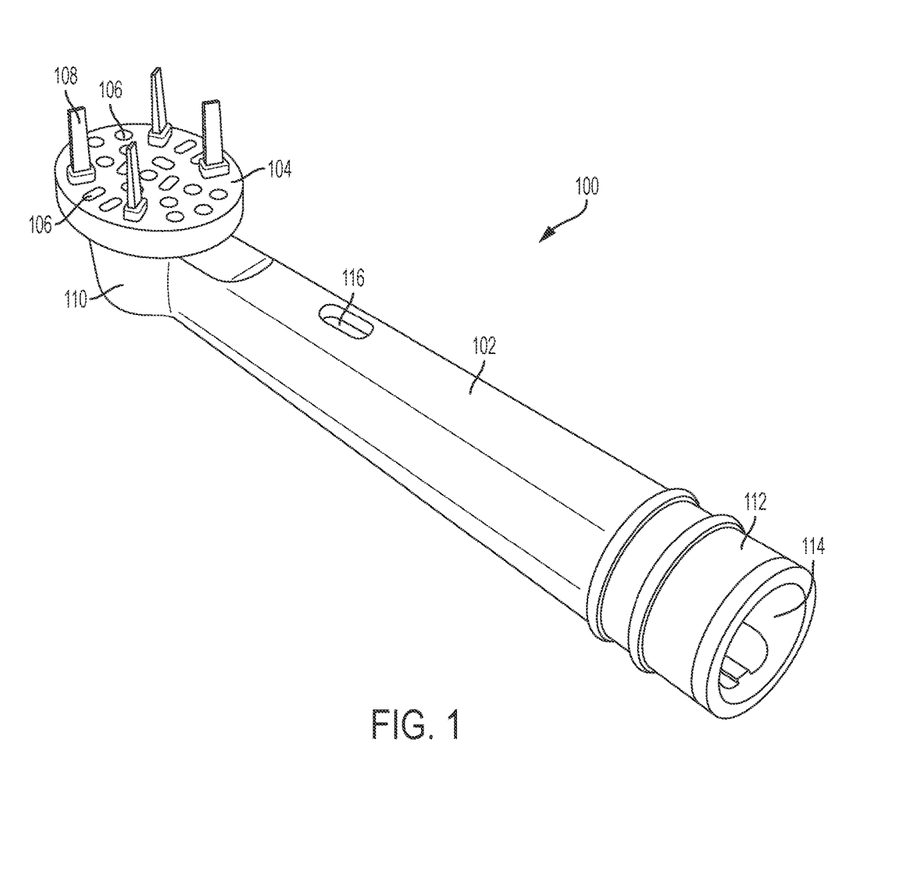
FIG. 1 depicts a perspective view of a toothbrush head according to some embodiments.

Referring to FIG. 1, in some embodiments, a brush head 100 is removable component attachable to a drive shaft of an electric toothbrush handle (not shown). Brush head 100 may be configured as an original component of an electric toothbrush assembly, or may be a separate, replacement component. The brush head 100 includes an elongated neck 102 having a proximal end portion 112 and a distal end portion 110, wherein the brush head 100 is couplable to an electric toothbrush handle at proximal end portion 112. At or near distal end portion 110, a bristle carrier 104 is disposed for rotatable and/or oscillatory motion about an axis transverse to a longitudinal axis of the neck 102. Neck 102 and bristle carrier 104 may be formed of various materials, but are preferably molded plastic or polyester materials, such as, for example, polyoxymethylene, polyvinylchloride, etc. Bristle carrier 104 includes a plurality of openings 106 configured to retain a plurality of flexible brush bristles (not shown) therein. The brush bristles may be retained in openings 106 through any appropriate retention method, including, but not limited to, weaving, tying, adhesive retention, welding, etc. Interposed between openings 106 are a plurality of semi-rigid flossing structures 108, configured to act in concert with the flexible brush bristles during use of the electric toothbrush. While four flossing structures 108 are shown in FIG. 1, it is to be understood that more or fewer flossing structures may be utilized on bristle carrier 104. Alternatively, bristle carrier 104 may omit the use of flossing structures 108 and only utilize brush bristles.

A sleeve 114 may be at least partially disposed within neck 102 at or near proximal end portion 112. As will be discussed further herein with reference to FIGS. 9A-9C, sleeve 114 is sized and shaped to create a close-fitting interface for the coupling of brush head 100 to the electric toothbrush handle. The interior size and contours of sleeve 114 are configured such that brush head 100 may be removably joined only to compatible electric toothbrush handles.

Neck 102 may also comprise one or more openings 116 along a length thereof. Opening(s) 116 are configured to allow water or other liquids to drain from within brush head 100. Furthermore, opening(s) 116 may also enable a user to view the movable components within brush head 100.

Figure 2:
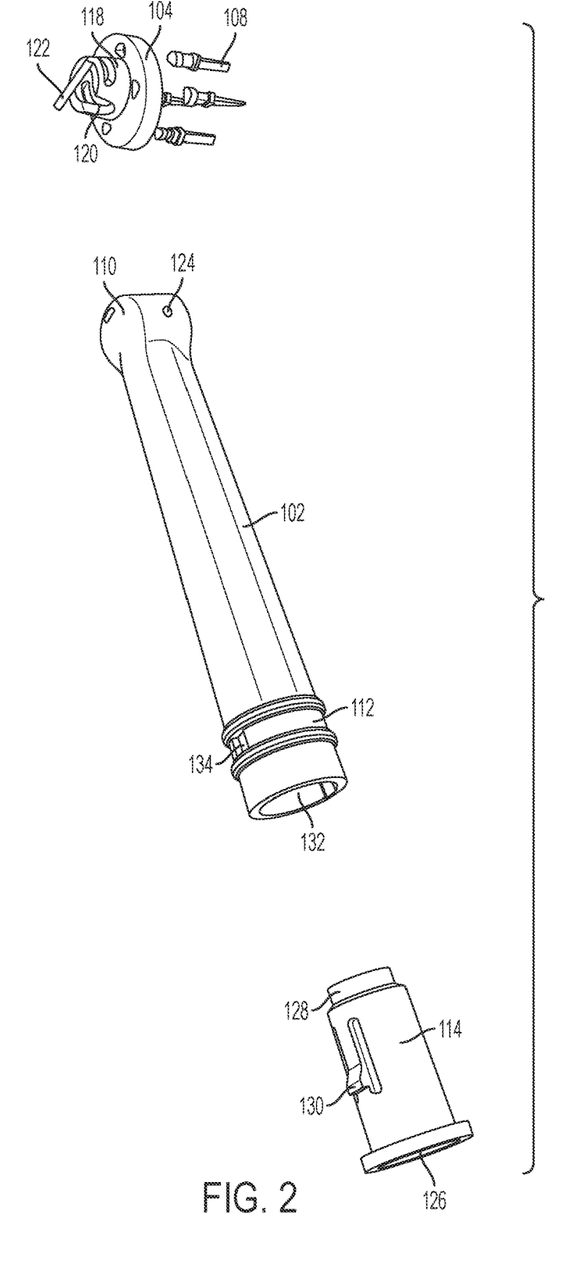
FIG. 2 is an exploded view of some components of the toothbrush head according to some embodiments.

Referring to FIG. 2, a partial exploded view of brush head 100 is shown. Bristle carrier 104 includes a substantially cylindrical carrier extension 118. Carrier extension 118 extends from a rear surface of bristle carrier 104, opposite of the brush bristles (not shown) and/or flossing structures 108. Carrier extension 118 may be molded together with bristle carrier 104. Alternatively, carrier extension 118 may be formed separately from bristle carrier 104 and coupled the rear surface of bristle carrier 104 via any appropriate means, including, for example, an adhesive, welding, etc. Formed in a lower portion of carrier extension 118 is a substantially U-shaped channel 120, wherein channel 120 is configured to open in a direction away from bristle carrier 104. While channel 120 is shown as being U-shaped, it is to be understood that channel 120 may be of any appropriate shape and/or depth, including, for example, V-shaped, semi-circular, square-shaped, etc.

Associated with bristle carrier 104 is a retention rod 122, which may be configured to retain bristle carrier 104 at distal end portion 110 of neck 102, while still allowing for rotational and/or oscillatory movement of bristle carrier 104. Specifically, retention rod 122 may pass through a pair of opposing slots formed within carrier extension 118, as will be described further hereinbelow. The respective ends of retention rod 122 may be affixed to the distal end portion 110 via, for example, a pair of holes 124 formed in the neck 102. Retention rod 122 may be formed of any appropriate material, such as, for example, steel, aluminum, plastic, etc.

As noted above with respect to FIG. 1, sleeve 114 may be slidably disposed within proximal end portion 112 of neck 102. Specifically, sleeve 114 is sized and contoured to fit within a proximal opening 132 of neck 102. Upon initial assembly of brush head 100, sleeve 114 may be configured to slidably travel in a distal direction upon insertion into proximal opening 132. After sliding a predetermined distance into proximal opening 132, a retention shoulder 130 extending from sleeve 114 is configured to mate with a retention opening 134 formed in proximal end portion 112 of neck 102. Retention shoulder 130 may be formed on sleeve 114 so as to be inwardly compressible, thereby allowing retention shoulder 130 to flex inwardly upon initial insertion into neck 102 until reaching retention opening 134. Upon reaching retention opening 134, retention shoulder 130 is configured to flex outwardly, thereby locking sleeve 114 within proximal opening 132 of neck 102. A lower rim 126 located at a proximal end of sleeve 114 may have a width larger than that of the sleeve 114 and thus be configured to interact with the proximal end of neck 102 so as to limit the insertion depth of sleeve 114 within neck 102. Furthermore, a cylindrical upper rim 128 located at a distal end of sleeve 114 is formed to provide an interface with moving components of brush head 100, as will be described further hereinbelow.

Figure 3:
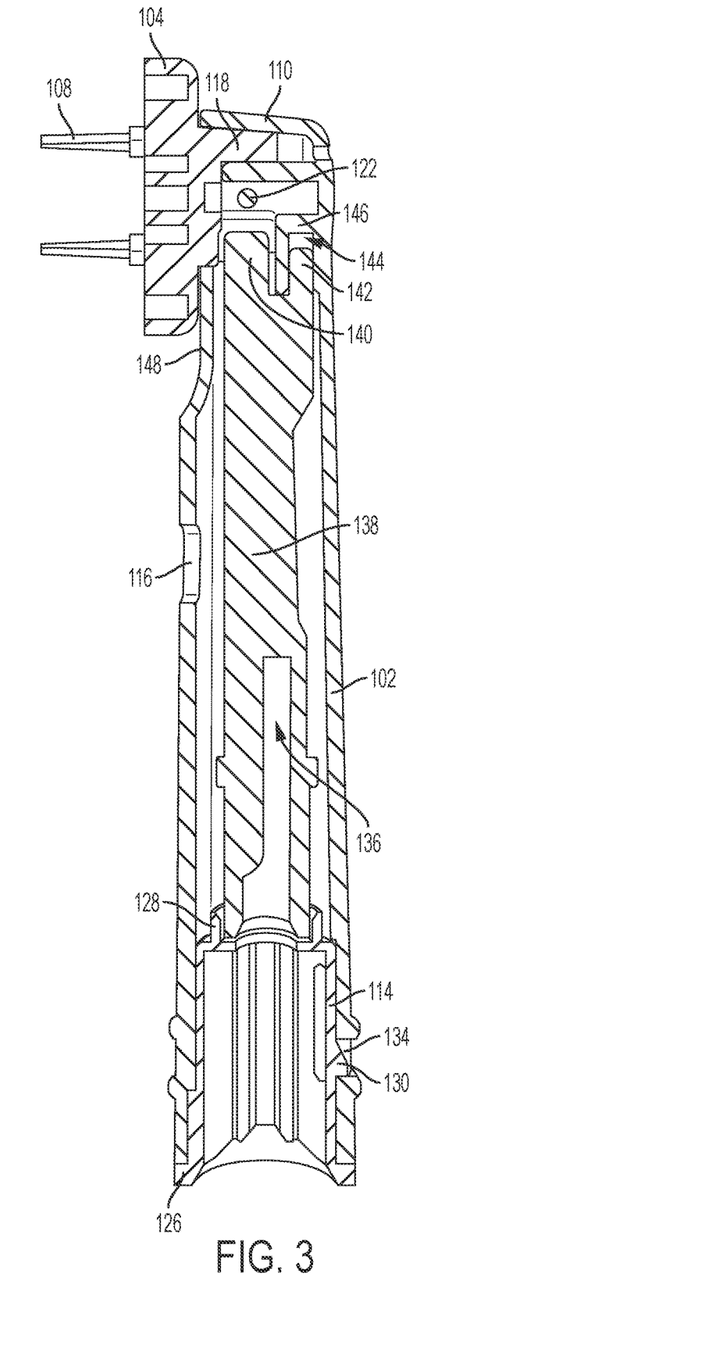
FIG. 3 is a side sectional view of the toothbrush head of according to the embodiments shown in FIG. 1.
Figure 4:
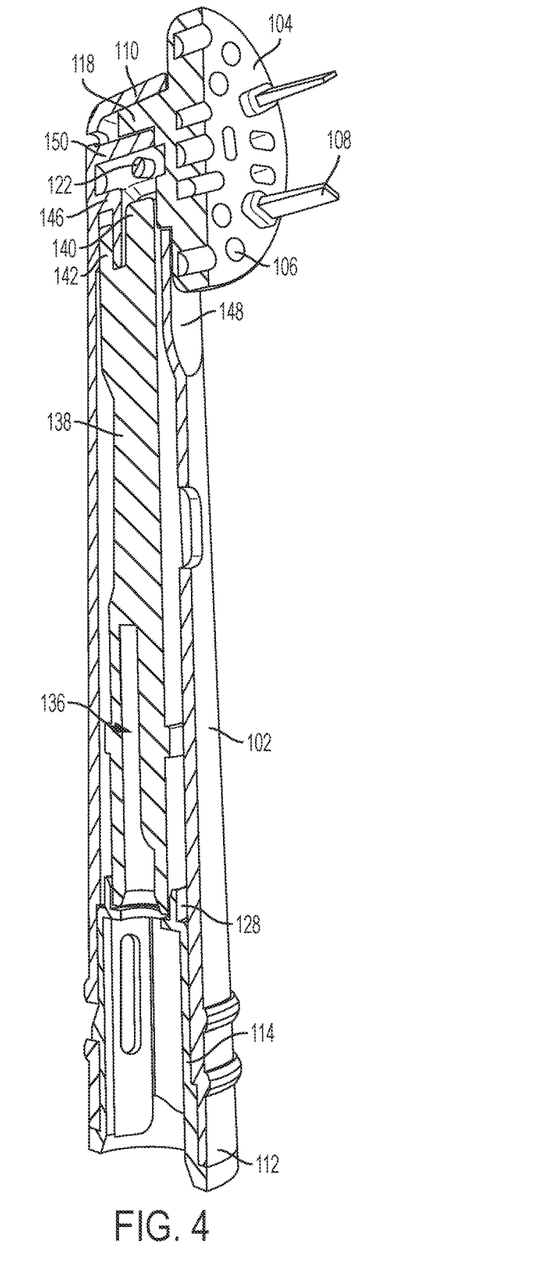
FIG. 4 is a perspective sectional view of the toothbrush head of according to the embodiments shown in FIG. 1.
Figure 5A:
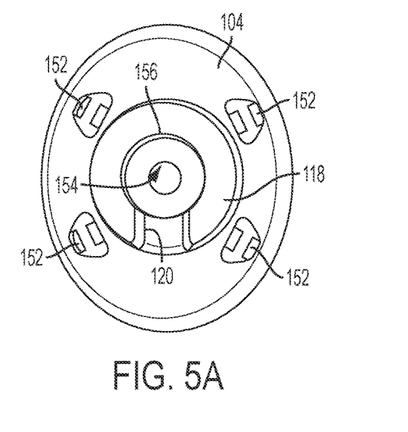
FIG. 5A is a rear view of a bristle carrier for use on a toothbrush head according to some embodiments.
Figure 5B:
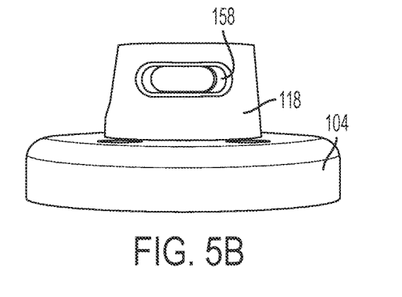
FIG. 5B is a right side view of the bristle carrier according to the embodiments shown in FIG. 5A.
Figure 5C:
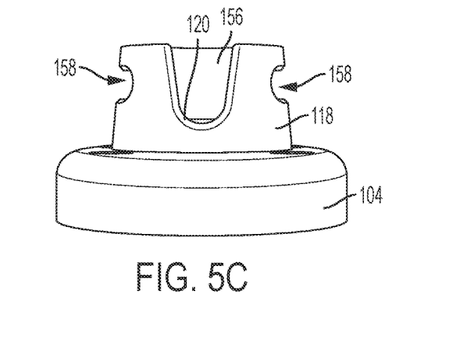
FIG. 5C is a bottom side view of the bristle carrier according to the embodiments shown in FIG. 5A.
Figure 5D:
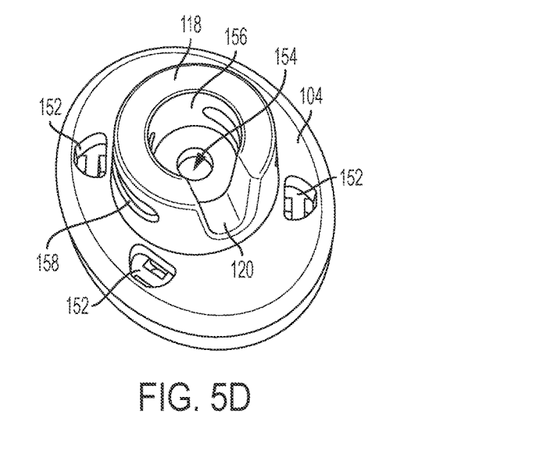
FIG. 5D is a rear perspective view of the bristle carrier according to the embodiments shown in FIG. 5A.

Referring now to FIG. 3 and FIG. 4, cross-sectional views of brush head 100, according to some embodiments, are shown. As described above, bristle carrier 104 is movably coupled to neck 102 so as to enable rotational and/or oscillatory motion about an axis perpendicular to the longitudinal axis of neck 102. A cut-away region 148 of neck 102 may be sized and configured to allow for unobstructed rotation and/or oscillation of bristle carrier 104. As shown in FIG. 4, carrier extension 118 is formed to fit closely around a substantially cylindrical neck hub 150 within distal end portion 110 of neck 102, yet still be at least partially rotatable around neck hub 150. In this way, bristle carrier 104 may be driven to rotate and/or oscillate with respect to neck 102 with reduced vibration as compared to conventional brush heads, as will be described further hereinbelow.

Movably housed within the interior of neck 102 is a brush shaft 138. Brush shaft 138 may be formed of any appropriate material but, in some embodiments, is formed as a single piece of molded plastic. A proximal end portion of brush shaft 138 may be movably retained within cylindrical rim 128 of sleeve 114 when sleeve 114 is inserted into neck 102, as described above. In this way, lateral and/or longitudinal movement of brush shaft 138 within neck 102 is restricted, but at least partial rotational movement of brush shaft 138 is permitted. A drive shaft opening 136 is formed within brush shaft 138 at a proximal end portion of brush shaft 138, wherein drive shaft opening 136 is sized and shaped to accept the drive shaft of an electric toothbrush handle when brush head 100 is attached to the electric toothbrush handle. The size and shape of drive shaft opening 136 may be specifically formed to accommodate only certain types of drive shafts, thereby ensuring that only compatible electric toothbrush handles be used in conjunction with brush head 100.

At the distal end of brush shaft 138 is a bristle carrier interface 140, as well as a pivot extension 142. As will be set forth in more detail hereinbelow, bristle carrier interface 140 is positioned and sized to interact with channel 120 of carrier extension 118 so as to translate motion from brush shaft 138 to bristle carrier 104 when the drive shaft of the electric toothbrush is operational. Pivot extension 142 extends from brush shaft 138 and is spaced apart from, but parallel to, the longitudinal axis of brush shaft 138. When brush shaft 138 is disposed within neck 102, pivot extension 142 is configured for insertion within a recess 144 of a pivot support 146 integrally formed in neck 102. As can be seen in FIG. 3, at least a portion of pivot support 146 is formed of an inner wall of neck 102. The recess 144 of pivot support 146 retains pivot extension 142 therein to limit axial movement of brush shaft 138, but allows at least partial rotational and/or oscillatory movement of brush shaft 138 relative to pivot support 146.

While pivot extension 142 is illustrated as being integrally formed with brush shaft 138, it is to be understood that pivot extension 142 may be separately formed from brush shaft 138 so as to be replaceable. Furthermore, pivot extension 142, if formed separately, may be formed of a different material than that which forms brush shaft 138. For example, pivot extension 142 may be made of steel, aluminum, or another metallic material, while the remainder of brush shaft 138 may be formed of a plastic material. Similarly, all or a portion of bristle carrier interface 140 may be formed integrally with brush shaft 138 or, alternatively, all or a portion of bristle carrier interface 140 may be formed separately and/or of a different material (e.g., a metallic material or other plastic material).

Referring now to FIGS. 5A-5D, the bristle carrier 104 and, specifically, the carrier extension 118 are shown in greater detail. Bristle carrier 104 comprises a plurality of flossing structure attachment openings 152 for the attachment of flossing structures 108 thereto. While four attachment openings 152 are shown in FIGS. 5A-5D, it is to be understood that more or fewer openings may be located on bristle carrier 104, directly proportional to the number of flossing structures 108 utilized.

Figure 7:
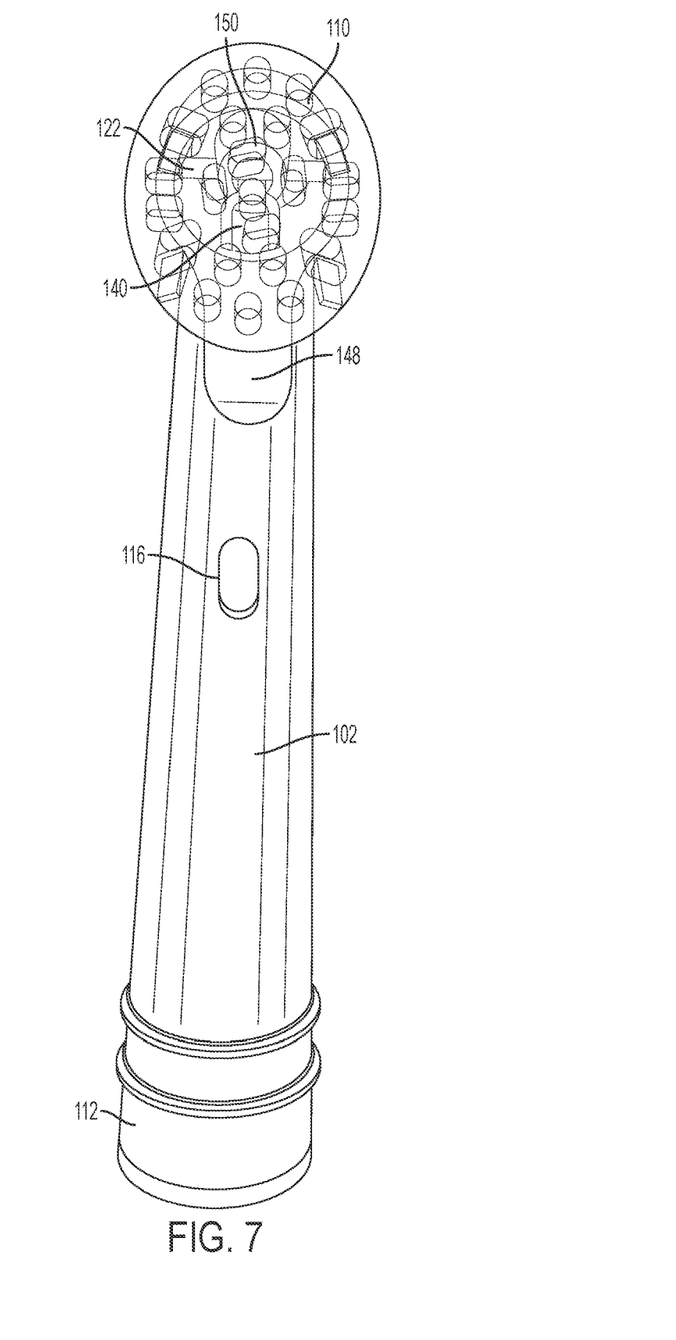
FIG. 7 is a front perspective view of a neck of the toothbrush head according to some embodiments.
Figure 8:
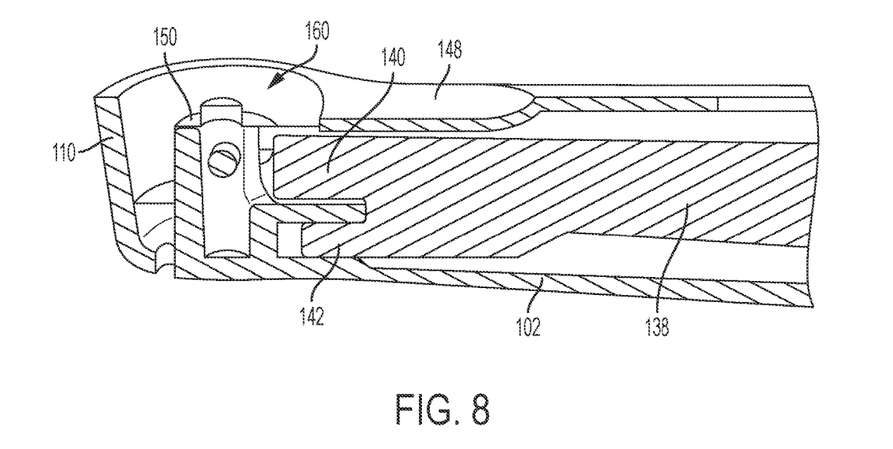
FIG. 8 is a partial side perspective view of the neck of the toothbrush head according to the embodiments shown in FIG. 7.

As described above, carrier extension 118 is sized and shaped to fit closely around the substantially cylindrical neck hub 150 within distal end portion 110 of neck 102. Specifically, an inner opening 154 of carrier extension 118 is sized to allow carrier extension 118 to fit around neck hub 150 within an opening 160 formed at distal end portion 110 of neck 102 when bristle carrier 104 is coupled to neck 102. FIGS. 7-8 provide further detail of neck hub 150 and opening 160 in accordance with some embodiments. An inner surface 156 of carrier extension 118 corresponds to an outer surface of neck hub 150, thereby reducing friction and associated vibration when bristle carrier 104 is driven by brush shaft 138.

Along opposing sides of carrier extension 118 are a pair of elongated slots 158. Elongated slots 158 are configured to receive respective ends of retention rod 122 therethrough so as to retain bristle carrier 104 on neck hub 150. Elongated slots 158 are sized and shaped to allow for constrained rotational and/or oscillatory motion of bristle carrier 104, while restricting and/or preventing axial movement of bristle carrier 104 when driven by brush shaft 138. The contours, length, and width of elongated slots 158 may be optimized to reduce friction and/or vibration of bristle carrier 104 when in use.

As noted above, a lower portion of carrier extension 118 includes a substantially U-shaped channel 120, wherein channel 120 is configured to open in a direction away from bristle carrier 104. While channel 120 is shown as being U-shaped, it is to be understood that channel 120 may be of any appropriate shape and/or depth, including, for example, V-shaped, semi-circular, square-shaped, etc.

Figure 6A:
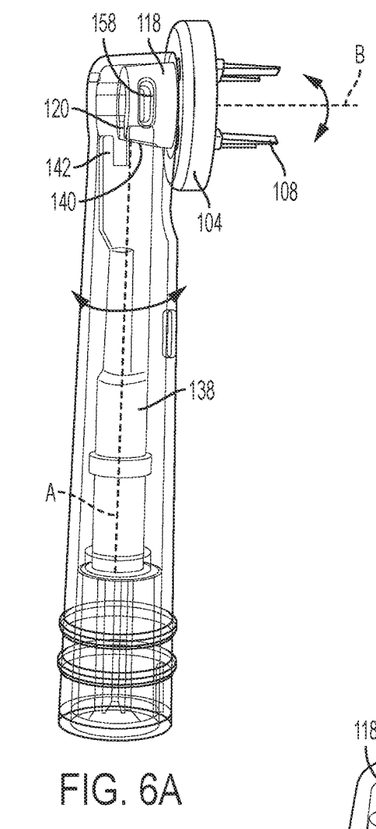
FIG. 6A is a side perspective view of a brush shaft and a bristle carrier according to some embodiments.
Figure 6B:
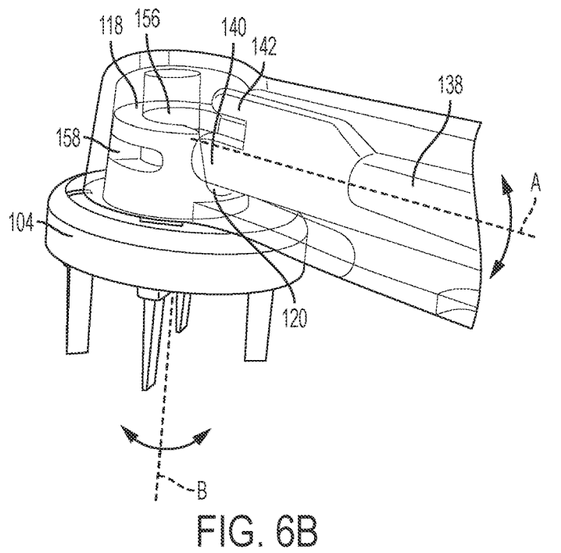
FIG. 6B is a partial side perspective view of the brush shaft and bristle carrier according to the embodiments shown in FIG. 6A.

Channel 120 may be of a sufficient width and depth to accommodate most or all of a distal portion of bristle carrier interface 140 on brush shaft 138. As illustrated in FIGS. 6A-6B, bristle carrier interface 140 is arranged at least partially along the longitudinal axis A of brush shaft 138, and bristle carrier interface 140 is configured to interact with at least a portion of channel 120. The bristle carrier interface 140 may be shaped to complement and/or correspond with the shape of channel 120. For instance, bristle carrier interface 140 may be egg-shaped or elliptical cross-sectional interface so as to complement the U-shaped surface of channel 120. However, it is to be understood that bristle carrier interface 140, like channel 120, may be any appropriate shape and/or size.

As brush shaft 138 is driven by the drive shaft of an electric toothbrush handle, brush shaft is configured to partially rotate and/or oscillate about pivot extension 142. Such rotation parallel to longitudinal axis A of brush shaft 138 causes bristle carrier interface 140 to interact with channel 120 of bristle carrier 104, thereby imparting partial rotation and/or oscillation of bristle carrier 104 about an axis B, which lies perpendicular to axis A. Accordingly, the user is provided with a movable bristle carrier capable of improving the cleaning of the user's teeth.

With brush shaft 138 subject to high-frequency rotational oscillation of the drive shaft of the electric toothbrush handle, bristle carrier interface 140 may be subject to high frictional forces when interacting with channel 120 of bristle carrier 104. However, because at least a portion of bristle carrier interface 140 is in-line with the longitudinal axis A of brush shaft 138, the torque and frictional forces experienced by bristle carrier interface 140 are reduced as compared to a similar interface entirely spaced apart from the longitudinal axis of a brush shaft. Accordingly, the wear characteristics and fatigue strength of the brush shaft 138 (particularly, the bristle carrier interface 140) and the bristle carrier 104 may be improved. Correspondingly, the vibration and/or noise caused by the interaction between brush shaft 138 and bristle carrier 104 may also be reduced, thereby providing for a more comfortable brushing experience for the user.

Figure 9A:
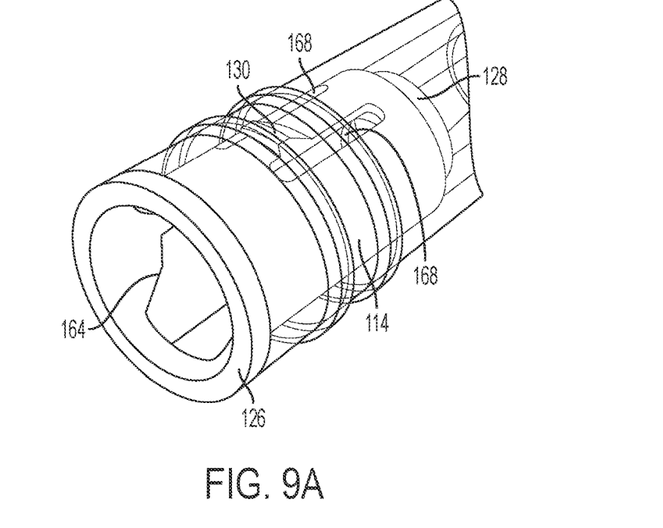
FIG. 9A is a perspective view of a retainer sleeve according to some embodiments.
Figure 9B:
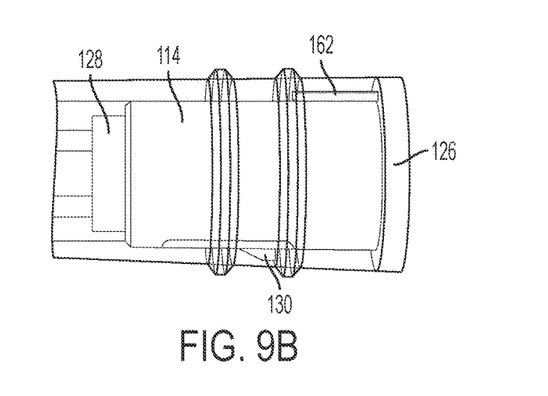
FIG. 9B is a side view of the retainer sleeve according to the embodiments shown in FIG. 9A.
Figure 9C:
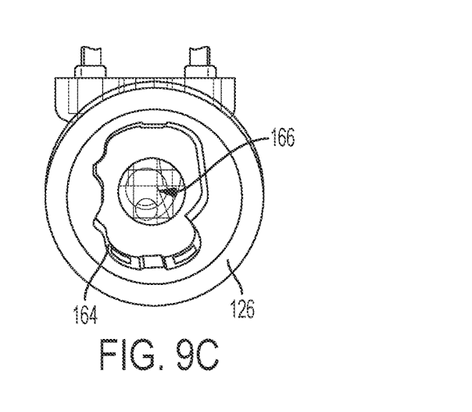
FIG. 9C is a bottom view of the retainer sleeve according to the embodiments shown in FIG. 9A.

Referring to FIGS. 9A-9C, further details of sleeve 114 in accordance with some embodiments are illustrated. As noted above, sleeve 114 may be at least partially disposed within neck 102 at or near proximal end portion 112. Sleeve 114 is sized and shaped to create a close-fitting interface for the coupling of brush head 100 to the electric toothbrush handle. As sleeve 114 is pressed into neck 102 during assembly, a key 162 extending from a surface of sleeve 114 is configured to mate with a complementary slot (not shown) formed in the interior surface of neck 102, which ensures that sleeve 114 may only be inserted in one orientation within neck 102. As sleeve 114 travels into neck 102, retention shoulder 130 is capable of deflecting inwardly due to a pair of slots 168 formed in sleeve 114, which provide for flexibility in the portion of the sidewall of sleeve 114 upon which retention shoulder 130 is molded or attached. As detailed above, retention shoulder 130 is configured to snap into a proximal opening 132 of neck 102, thereby retaining sleeve 114 within neck 102.

A distal end portion of sleeve 114 includes an opening 166 formed therein, wherein opening 166 allows a drive shaft of an electric toothbrush to pass therethrough for mating with the brush shaft 138 when brush head 100 is coupled to a compatible electric toothbrush handle. Furthermore, a contoured inner surface 164 within sleeve 114 may be provided in some embodiments, which may ensure that brush head 100, when incorporating sleeve 114, is only compatible and usable in a specific orientation with electric toothbrush handles having a corresponding connection interface. The fit between sleeve 114 and the connection interface of a compatible electric toothbrush handle is preferably a friction fit, which should allow for both effective coupling yet simple removal of the brush head 100.

The various embodiments disclosed in this document provide advantages over the prior art, whether standalone or combined. For example, the orientation and/or shape of the bristle carrier interface on the brush shaft may help to provide for reduced vibration and/or noise during operation, and also provides for reduced wear and increased fatigue strength of the brush shaft. Further, multiple engagements of various parts inside the neck, the coupling of the brush shaft and the bristle carrier, and the coupling of the neck and the sleeve all may improve the stability of the brush head as it is operating under the high speed vibrations of the motor inside the handle. Further, the manufacture of the toothbrush head may be simplified, as all the parts can be made of plastic or polyester materials, and without complex linkages.

Other advantages of the present disclosure can be apparent to those skilled in the art from the foregoing specification. Accordingly, it will be recognized by those skilled in the art that changes or modifications may be made to the above-described embodiments without departing from the broad inventive concepts of the disclosure. It should therefore be understood that this disclosure is not limited to the particular embodiments described herein, but is intended to include all changes and modifications that are within the scope and spirit of the disclosure as defined in the claims.

The invention claimed is:

1. A removable toothbrush head comprising:
   a bristle carrier, wherein the bristle carrier is configured to retain a plurality of brush bristles thereon;
   an elongated neck having a proximal end portion and a distal end portion, wherein the proximal end portion of the elongated neck comprises an opening formed therein for connection of the elongated neck to an electric toothbrush handle, and wherein the distal end portion of the elongated neck comprises a neck hub positioned traverse to a longitudinal axis of the elongated neck and configured to rotatably support the bristle carrier;
   a brush shaft disposed longitudinally within the elongated neck, wherein the brush shaft is configured to be removably couplable to a drive shaft of the electric toothbrush handle at an opening located within a proximal end portion of the brush shaft, and further wherein the brush shaft is configured to interact with the bristle carrier at a distal end portion of the brush shaft, the distal end portion of the brush shaft comprising:
      a pivot extension extending from the distal end portion of the brush shaft and spaced apart from the longitudinal axis of the brush shaft, the pivot extension pivotally couplable to a pivot support within the distal end portion of the elongated neck so as to enable at least partial rotational motion of the brush shaft about the pivot extension, and
      a bristle carrier interface positioned at least partially along the longitudinal axis of the brush shaft, the bristle carrier interface configured to interact with the bristle carrier to cause partial rotational motion of the bristle carrier upon the neck hub when the brush
shaft is driven by the drive shaft of the electric toothbrush handle; and
a sleeve inserted into the opening formed in the proximal end portion of the elongated neck, wherein the sleeve is configured to receive and guide the drive shaft of the electric toothbrush handle into the opening formed in the proximal end of the brush shaft, and
wherein the sleeve comprises a deflectable retention shoulder, the deflectable retention shoulder configured to mate with a retention opening formed in the elongated neck when the sleeve is inserted into the opening formed in the proximal end portion of the elongated neck.

2. The removable toothbrush head of claim 1, wherein the sleeve comprises a cylindrical rim formed on a distal end portion thereof, wherein the cylindrical rim is configured to movably retain a proximal end portion of the brush shaft therein.

3. The removable toothbrush head of claim 1, wherein the bristle carrier comprises a carrier extension extending from a surface opposite the plurality of brush bristles, wherein the carrier extension comprises a channel sized and shaped to interact with the bristle carrier interface of the brush shaft.

4. The removable toothbrush head of claim 3, wherein the carrier extension comprises an inner opening and an inner surface configured to allow the carrier extension to fit over an outer surface of the neck hub.

5. The removable toothbrush head of claim 3, wherein the carrier extension is substantially cylindrical.

6. The removable toothbrush head of claim 3, wherein the channel formed in the carrier extension is a U-shaped channel.

7. The removable toothbrush head of claim 6, wherein the U-shaped channel is sized and contoured to receive a distal end portion of the bristle carrier interface.

8. The removable toothbrush head of claim 3, further comprising a retention rod extending at least partially through the distal end portion of the elongated neck and the neck hub, wherein the carrier extension further comprises a pair of elongated slots configured to receive the retention rod so as to enable restricted rotational motion of the bristle carrier about the neck hub.

9. The removable toothbrush head of claim 1, wherein the brush shaft is formed as a single piece.

10. The removable toothbrush head of claim 9, wherein the brush shaft is formed of a molded plastic material.

11. The removable toothbrush head of claim 1, wherein the bristle carrier interface of the brush shaft is one of an egg-shaped cross-sectional interface or an elliptical-shaped cross-sectional interface.

12. The removable toothbrush head of claim 1, wherein the pivot support within the distal end portion of the elongated neck is at least partially formed along an inner wall of the elongated neck.

13. The removable toothbrush head of claim 1, wherein the elongated neck comprises at least one hole on a surface thereof to facilitate the draining of water from within the elongated neck.

14. The removable toothbrush head of claim 1, wherein the bristle carrier comprises at least one semi-rigid flossing structure extending therefrom.

* * * * *